(12) United States Patent
Wilk et al.

(10) Patent No.: US 8,309,594 B2
(45) Date of Patent: Nov. 13, 2012

(54) PURIFICATION OF PROGESTERONE RECEPTOR MODULATORS

(75) Inventors: Bogdan Kazimierz Wilk, New City, NY (US); Arkadiy Zinoviy Rubezhov, West Nyack, NY (US); Anthony Francis Hadfield, Ruskin, FL (US); Jean Louise Helom, Hillsdale, NJ (US)

(73) Assignee: Wyeth LLC, Madison, NJ (US)

( * ) Notice: Subject to any disclaimer, the term of this patent is extended or adjusted under 35 U.S.C. 154(b) by 760 days.

(21) Appl. No.: 12/369,775

(22) Filed: Feb. 12, 2009
(Under 37 CFR 1.47)

(65) Prior Publication Data
US 2009/0143577 A1    Jun. 4, 2009

Related U.S. Application Data

(62) Division of application No. 11/113,730, filed on Apr. 25, 2005, now Pat. No. 7,514,466.

(60) Provisional application No. 60/565,659, filed on Apr. 27, 2004.

(51) Int. Cl.
*A01N 43/318* (2006.01)
*A61K 31/40* (2006.01)

(52) U.S. Cl. .................... 514/409; 514/414; 514/421

(58) Field of Classification Search ............. 514/409, 514/414, 421
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,185,009 A | 1/1980 | Idel et al. | |
| 4,295,987 A | 10/1981 | Parks | |
| 4,540,564 A | 9/1985 | Bodor | |
| 4,829,070 A | 5/1989 | Bodor | |
| 4,959,217 A | 9/1990 | Sanders et al. | |
| 5,010,079 A | 4/1991 | Manoury et al. | |
| 5,087,618 A | 2/1992 | Bodor | |
| 5,171,851 A | 12/1992 | Kim et al. | |
| 5,266,325 A | 11/1993 | Kuzma et al. | |
| 5,273,752 A | 12/1993 | Ayer et al. | |
| 5,292,515 A | 3/1994 | Moro et al. | |
| 5,389,623 A | 2/1995 | Bodor | |
| 5,525,727 A | 6/1996 | Bodor | |
| 5,663,431 A | 9/1997 | Di Malta et al. | |
| 5,756,127 A | 5/1998 | Grisoni et al. | |
| 5,817,343 A | 10/1998 | Burke | |
| 5,854,388 A | 12/1998 | Harding et al. | |
| 5,874,430 A | 2/1999 | Christ et al. | |
| 6,306,851 B1 | 10/2001 | Santilli et al. | |
| 6,319,912 B1 | 11/2001 | Grubb et al. | |
| 6,329,416 B1 | 12/2001 | Grubb et al. | |
| 6,339,098 B1 | 1/2002 | Collins et al. | |
| 6,355,648 B1 | 3/2002 | Fensome et al. | |
| 6,358,947 B1 | 3/2002 | Zhi et al. | |
| 6,358,948 B1 | 3/2002 | Zhang et al. | |
| 6,369,056 B1 | 4/2002 | Zhang et al. | |
| 6,380,178 B1 | 4/2002 | Grubb et al. | |
| 6,380,235 B1 | 4/2002 | Zhang et al. | |
| 6,391,907 B1 | 5/2002 | Fensome et al. | |
| 6,399,593 B1 | 6/2002 | Grubb et al. | |
| 6,407,101 B1 | 6/2002 | Collins et al. | |
| 6,417,214 B1 | 7/2002 | Ullrich et al. | |
| 6,423,699 B1 | 7/2002 | Grubb et al. | |
| 6,436,929 B1 | 8/2002 | Zhang et al. | |
| 6,441,019 B2 | 8/2002 | Santilli et al. | |
| 6,444,668 B1 | 9/2002 | Grubb et al. | |
| 6,462,032 B1 | 10/2002 | Grubb et al. | |
| 6,466,648 B1 | 10/2002 | Ikeno et al. | |
| 6,498,154 B1 | 12/2002 | Grubb et al. | |
| 6,503,939 B2 | 1/2003 | Grubb et al. | |
| 6,509,334 B1 | 1/2003 | Zhang et al. | |
| 6,521,657 B2 | 2/2003 | Fensome et al. | |
| 6,544,970 B2 | 4/2003 | Grubb et al. | |
| 6,562,857 B2 | 5/2003 | Collins et al. | |
| 6,566,358 B2 | 5/2003 | Zhang et al. | |
| 6,583,145 B1 | 6/2003 | Fensome et al. | |

(Continued)

FOREIGN PATENT DOCUMENTS

CA    2095587    2/2000

(Continued)

OTHER PUBLICATIONS

Office Action dated Feb. 8, 2011 issued in Japanese Patent Application No. 2007-510848.
Office Action dated Aug. 31, 2010 issued in Australian Patent Application No. 2005237520.
Office Action dated Dec. 26, 2008 issued in Chinese Patent Application No. 200580013278.
Office Action dated Jul. 22, 2010 issued in Indian Patent Application No. 2984/KOLNP/2006.
Singh et al., "Novel cAMP PDE III inhibitors: imidazo[4,5-b]pyridin-2(3H)-ones and thiazolo[4,5-b]pyridin-2(3H)-ones and their analogs", J. Med. Chem. Jan. 21, 1994 37(2): 248-254.

(Continued)

*Primary Examiner* — Erich A Leeser
(74) *Attorney, Agent, or Firm* — Howson & Howson LLP

(57) ABSTRACT

Methods for purifying a compound of formula I are provided, wherein A, B, X, Q, and $R^1$ are defined herein.

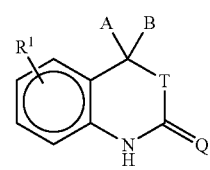

The methods include mixing the compound of formula I and a solvent; adding a base to the solvent; and precipitating purified compound of formula I.

21 Claims, No Drawings

U.S. PATENT DOCUMENTS

| | | | |
|---|---|---|---|
| 6,608,068 | B2 | 8/2003 | Fensome et al. |
| 6,693,103 | B2 | 2/2004 | Zhang et al. |
| 6,713,478 | B2 | 3/2004 | Zhang et al. |
| 6,759,408 | B2 | 7/2004 | Grubb et al. |
| 6,794,373 | B2 | 9/2004 | Grubb et al. |
| 6,835,744 | B2 | 12/2004 | Ullrich et al. |
| 6,841,568 | B2 | 1/2005 | Fensome et al. |
| 6,946,454 | B2 | 9/2005 | Fensome et al. |
| 6,982,261 | B2 | 1/2006 | Collins et al. |
| 7,081,457 | B2 | 7/2006 | Zhang et al. |
| 7,084,168 | B2 | 8/2006 | Fensome et al. |
| 7,119,086 | B2 | 10/2006 | Di Malta et al. |
| 7,488,822 | B2 | 2/2009 | Zhang et al. |
| 7,514,466 | B2 * | 4/2009 | Wilk et al. .......... 514/409 |
| 2002/0111355 | A1 | 8/2002 | Zhang et al. |
| 2002/0115853 | A1 | 8/2002 | Zhang et al. |
| 2005/0250766 | A1 | 11/2005 | Wilk et al. |
| 2007/0213526 | A1 | 9/2007 | Levent et al. |
| 2011/0178311 | A1 * | 7/2011 | Levent et al. .......... 548/411 |

FOREIGN PATENT DOCUMENTS

| | | | |
|---|---|---|---|
| EP | 0 300 614 | | 1/1989 |
| EP | 314206 | | 5/1989 |
| EP | 354094 | | 2/1990 |
| EP | 636608 | | 2/1995 |
| EP | 1253145 | | 10/2002 |
| GB | 1135899 | | 12/1968 |
| JP | S51-068566 | | 6/1976 |
| JP | S51-092893 | | 8/1976 |
| JP | 07281374 | | 10/1995 |
| JP | 11095372 | | 4/1999 |
| JP | 2001031656 | | 2/2001 |
| JP | 2002-543155 | | 12/2002 |
| JP | 2002-543158 | | 12/2002 |
| JP | 2002-543192 | | 12/2002 |
| WO | WO-92/21656 | | 12/1992 |
| WO | WO-97/03066 | | 1/1997 |
| WO | WO-98/44964 | | 10/1998 |
| WO | WO-98/51676 | | 11/1998 |
| WO | WO-99/62900 | | 12/1999 |
| WO | WO 00/06167 | * | 11/2000 |
| WO | WO 00/66164 | | 11/2000 |
| WO | WO 00/66167 | | 11/2000 |
| WO | WO-00/66555 | | 11/2000 |
| WO | WO-00/66570 | | 11/2000 |
| WO | WO-01/57007 | | 8/2001 |
| WO | WO-02/16333 | | 2/2002 |
| WO | WO-02/32465 | | 4/2002 |
| WO | WO-02/102783 | | 12/2002 |
| WO | WO-03/008407 | | 1/2003 |
| WO | WO-03/044016 | | 5/2003 |
| WO | WO-2004/000227 | | 12/2003 |
| WO | WO-2004/000230 | | 12/2003 |

OTHER PUBLICATIONS

Testa et al., "Prodrugs revisited: The "Ad Hoc" approach as a complement to ligand design", Med. Res.Rev. May 1996 16(3):233-241.

Bacheler et al., "Genotypic correlates of phenotypic resistance to efavirenz in virus isolates from patients failing nonnucleoside reverse transcriptase inhibitor therapy", J. Virol. Jun. 2001 75(11):4999-5008.

Barreiro et al. "Different degree of immune recovery using antiretroviral regimens with protease inhibitors or non-nucleosides", AIDS Jan. 25, 2002 16(2)245-249.

Cocuzza et al., "4,1-Benzoxazepinone analogues of efavirenz (Sustiva) as HIV-1 reverse transcriptase inhibitors", Bioorg. Med. Chem. Lett. Jun. 4, 2001 11(11)1389-1392.

Harrigan et al., "Extent of cross-resistance between agents used to treat human immunodeficiency virus type 1 infection in clinically derived isolates", Antimicrob. Agents & Chem. Mar. 2002 46(3):909-912.

Isaka et al., "Isolation and characterization of simian immunodeficiency virus variants that are resistant to nonnucleoside reverse transcriptase inhibitors", Arch. Virol. Dec. 2000 145(12):2481-2492.

Markwalder et al., "Synthesis and biological activities of potential metabolites of the non-nucleoside reverse transcriptase inhibitor efavirenz", Bioorg. Med. Chem. Lett. Mar. 12, 2001 11(5):619-622.

Mewshaw et al., "Dioxolane guanosine, the active form of the prodrug diaminopurine dioxolane, is a potent inhibitor of drug-resistant HIV-1 isolates from patients for whom standard nucleoside therapy fails", JAIDS Jan. 1, 2002 29(1):11-20.

Palmer et al., "Highly drug-resistant HIV-1 clinical isolates are cross-resistant to many antiretroviral compounds in current clinical development", AIDS Apr. 16, 1999 13(6):661-667.

Paolucci et al., "Analysis of HIV drug-resistant quasispecies in plasma, peripheral blood mononuclear cells and viral isolates from treatment-naive and HAART patients", J. Med. Virol. Oct. 2001 65(2):207-217.

Somei et al., "A Novel Synthetic Method of Pyrrolo[2,3-b]indoles and Its Application to the Synthesis of (±)-Debromofiustramine B", Heterocycles Dec. 1, 1997 45(12):2327-2330.

Kawabe et al., English language abstract of JP 11-095372, Apr. 9, 1999.

Michigami et al., English language abstract of JP 07-281374, Oct. 27, 1995.

Hanaki et al., English language abstract of JP 2001-031656, Feb. 6, 2001.

Manoury et al., English language abstract of EP 0 354 094, Feb. 7, 1990.

Gautier et al., English language abstract of WO 99/62900, Dec. 9, 1999.

Di Malta et al., English language abstract of EP 0 636,608, Feb. 1, 1995.

Di Malta et al., English language abstract of WO 03/008407, Jan. 30, 2003.

Felix et al., "Leukemia in Infants", The Oncologist, 4(3):225-240, Jun. 1999.

Office Action dated Sep. 28, 2011 issued in Canadian Patent Application No. 2,563,063.

Response dated Mar. 27, 2012 to the Office Action dated Sep. 28, 2011 issued in Canadian Patent Application No. 2,563,063.

Response dated Dec. 9, 2011 to the Office Action dated Aug. 3, 2010 issued in Australian Patent Application No. 2005237520.

English translation of an Office Action dated Nov. 15, 2011 issued in Japanese Patent Application No. 2007-510848.

Response dated Jan. 17, 2011 to the Office Action dated Jul. 22, 2010 issued in Indian Patent Application No. 2984/KOLNP/2006.

* cited by examiner

PURIFICATION OF PROGESTERONE RECEPTOR MODULATORS

CROSS-REFERENCE TO RELATED APPLICATIONS

This application is a divisional of U.S. patent application Ser. No. 11/113,730, filed Apr. 25, 2005, which claims the benefit under 35 USC 119(e) of prior U.S. Provisional Patent Application No. 60/565,659, filed Apr. 27, 2004, now expired.

BACKGROUND OF THE INVENTION

The present invention relates to the production of progesterone receptor modulators.

The purification of progesterone receptor (PR) modulators can be achieved by recrystallization using organic solvents. However, since many PR modulators have poor solubilities in organic solvents, recrystallization requires large volumes of the organic solvents to dissolve the PR modulators, thus making the purification less economical.

What is needed in the art are alternate methods for purifying progesterone receptor modulators.

SUMMARY OF THE INVENTION

In one aspect, the present invention provides a method for purifying indolone, indol-thione, indol-ylidene cyanamide, benzoxazinone, benzoxazin-thione, benzoxazin-ylidene cyanamide, benzothiazinone, benzothiazine-thione, benzothiazin-ylidene cyanamide compounds, or derivatives thereof.

In a further aspect, the present invention provides a method for purifying indol-2-one, indol-2-thione, indol-2-ylidene cyanamide, benzoxazin-2-one, benzoxazin-2-thione, benzoxazin-2-ylidene cyanamide, benzothiazin-2-one, benzothiazine-2-thione, benzothiazin-2-ylidene cyanamide compounds, or derivatives thereof.

In still a further aspect, these compounds are progesterone receptor modulators.

In another aspect, the invention provides a method for purifying a compound of formula I:

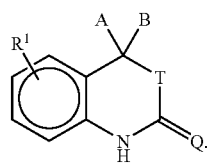

I

Other aspects and advantages of the present invention are described further in the following detailed description of the preferred embodiments thereof.

DETAILED DESCRIPTION OF THE INVENTION

The present invention provides methods for the purification of progesterone receptor modulators, including agonists and antagonists, and their intermediates. In one embodiment, the progesterone receptor modulators prepared according to the present invention contain an acidic hydrogen atom. In a further embodiment, the progesterone receptor modulators prepared according to the present invention contain an acidic N—H group. In still further embodiments, the compounds are indolone, indol-thione, indol-ylidene cyanamide, benzoxazinone, benzoxazin-thione, benzoxazin-ylidene cyanamide, benzothiazinone, benzothiazine-thione, benzothiazin-ylidene cyanamide compounds, or derivatives thereof, or indol-2-one, indol-2-thione, indol-2-ylidene cyanamide, benzoxazin-2-one, benzoxazin-2-thione, benzoxazin-2-ylidene cyanamide, benzothiazin-2-one, benzothiazine-2-thione, benzothiazin-2-ylidene cyanamide compounds, or derivatives thereof.

The inventors have found that by treating a crude form of a compound of formula I with a base to form a basic salt, the basic salt can be converted to a purified form of the same compound. See, Scheme 1, wherein A, B, T, Q, and $R^1$ are defined below.

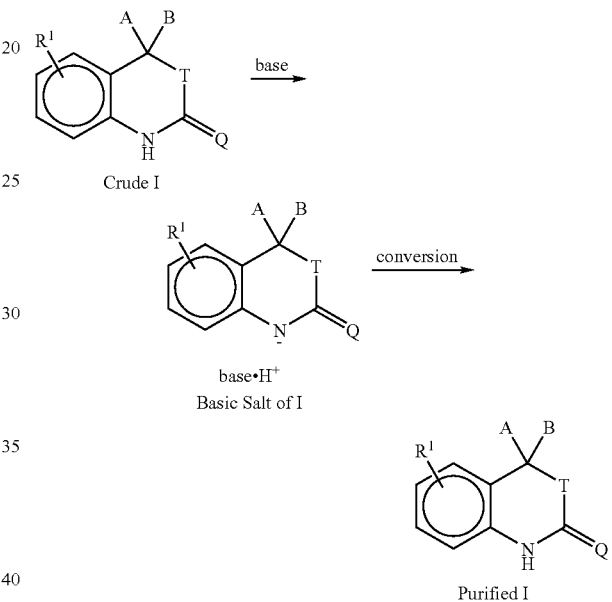

Scheme 1

I. DEFINITIONS

The term "alkyl" is used herein to refer to both straight- and branched-chain saturated aliphatic hydrocarbon groups having 1 to about 10 carbon atoms, or 1 to about 6 carbon atoms. The term "alkenyl" is used herein to refer to both straight- and branched-chain alkyl groups having one or more carbon-carbon double bonds and containing about 2 to about 10 carbon atoms. In one embodiment, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. In one embodiment, the term alkynyl refers to an alkyl group having 1 or 2 carbon-carbon triple bonds and having 2 to about 6 carbon atoms.

The term "cycloalkyl" is used herein to refer to an alkyl group, as previously described, that is cyclic in structure and has about 3 to about 10 carbon atoms, about 4 to about 8 carbon atoms, or about 5 to about 8 carbon atoms.

The terms "substituted alkyl", "substituted alkenyl", "substituted alkynyl", and "substituted cycloalkyl" refer to alkyl, alkenyl, alkynyl, and cycloalkyl groups, respectively, having one or more substituents the same or different including, without limitation, halogen, CN, OH, NO$_2$, amino, aryl, heterocyclic, alkoxy, aryloxy, alkylcarbonyl, alkylcarboxy, and arylthio, which groups can be optionally substituted. These substituents can be attached to any carbon of an alkyl, alkenyl, or alkynyl group provided that the attachment constitutes a stable chemical moiety.

The term "aryl" as used herein as a group or part of a group refers to an aromatic system which can include a single ring or multiple aromatic rings fused or linked together where at least one part of the fused or linked rings forms the conjugated aromatic system e.g. having 6 to 14 carbon atoms. The aryl groups can include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents the same or different including halogen, CN, OH, NO$_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to about 4 substituents.

The term "heterocyclic" as used herein refers to a stable 4- to 10-membered monocyclic or multicyclic heterocyclic ring which is saturated, partially unsaturated, or wholly unsaturated. The heterocyclic ring has carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring, e.g. of 6 to 14 carbon atoms. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, azepinyl, and carbazolyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents the same or different including halogen, CN, OH, NO$_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted heterocyclic group is substituted with 1 to about 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" includes hydroxyalkyl and as used herein refers to the alkylOH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" includes "alkylamino" and as used herein refers to both secondary and tertiary amines where the point of attachment is through the nitrogen-atom and the alkyl groups are optionally substituted. The alkyl groups can be the same or different.

The term "thioalkoxy" or "thioalkyl" as used herein refers to the S(alkyl) group, where the point of attachment is through the sulfur-atom and the alkyl group is optionally substituted.

The term "halogen" as used herein refers to Cl, Br, F, or I groups.

The term "ester" as used herein refers to a C(O)O, where the points of attachment are through both the C-atom and O-atom. One or both oxygen atoms of the ester group can be replaced with a sulfur atom, thereby forming a "thioester", i.e., a C(O)S, C(S)O or C(S)S group.

A "base" useful in the invention is a chemical compound having a pKa greater than 16 that is capable of abstracting an acidic hydrogen atom bound to a molecule.

An "acid" useful in the invention is a chemical compound having a pKa of less than 16. A number of acids can be utilized according to the present invention and include water, mineral acids, and organic acids such as hydrochloric acid, acetic acid, and solutions containing hydrochloric acid or acetic acid, among others. In one embodiment, the acid is aqueous hydrochloric acid or aqueous acetic acid.

The term "purified" or "pure" as used herein refers to a compound that contains less than about 10% impurities. In one embodiment, the term "purified" or "pure" refers to a compound that contains less than about 5% impurities, less than about 2% impurities, or less than about 1% impurities. The term "purified" or "pure" can also refer to a compound that contains about 0% impurities.

The term "crude" as used herein refers to a compound that contains greater than about 10% impurities. In one embodiment, the term "crude" refers to a compound that contains greater than about 5% impurities, greater than about 2% impurities, or greater than about 1% impurities. The impurities that can be present in a crude sample can include unused starting materials or undesirable side products formed during the reaction to form the crude compound. In one embodiment, such impurities are present as solids. The impurities can also include solvents that are present or trapped in the crude compound.

By the term "dry" or "drying" is meant a procedure by which entrapped solvents, including organic solvents, purifying solvents, solubilizing solvents, or water, or volatile solids are removed from a sample.

The term "electron withdrawing group" as used herein is meant to describe a chemical substituent that withdraws electrons from the chemical group to which it is attached. Examples of electron withdrawing groups include, without limitation, CN, $SO_3H$, $CO_2H$, $CO_2R$, CHO, COR, $NO_2$, $NR_3^+$, $CF_3$, or $CCl_3$. In one embodiment, the electron withdrawing group is CN.

II. METHOD OF THE INVENTION

The present invention therefore provides methods for purifying indolone, indol-thione, indol-ylidene cyanamide, benzoxazinone, benzoxazin-thione, benzoxazin-ylidene cyanamide, benzothiazinone, benzothiazine-thione, benzothiazin-ylidene cyanamide compounds, or derivatives thereof. In a further embodiment, indol-2-one, indol-2-thione, indol-2-ylidene cyanamide, benzoxazin-2-one, benzoxazin-2-thione, benzoxazin-2-ylidene cyanamide, benzothiazin-2-one, benzothiazine-2-thione, benzothiazin-2-ylidene cyanamide compounds, or derivatives thereof, are prepared according to the present invention.

In one embodiment, the present invention provides methods for purifying compounds of formula I.

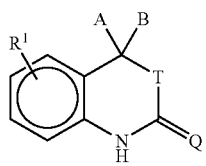

I wherein, A and B are independently selected from H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$. Alternatively, A and B are joined to form a ring including (i) a carbon-based 3 to 8 membered saturated spirocyclic ring; (ii) a carbon-based 3 to 8 membered spirocyclic ring containing in its backbone one or more carbon-carbon double bonds; or (iii) a 3 to 8 membered heterocyclic ring containing in its backbone one to three heteroatoms selected from the group consisting of O, S and N. The rings are optionally substituted by from 1 to 4 groups independently selected from among fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), or $N(C_1$ to $C_6$ alkyl$)_2$. In one embodiment, A and B are $C_1$ to $C_6$ alkyl or are fused to form a carbon-based saturated spirocyclic ring. $R^A$ is selected from among H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, or substituted $C_1$ to $C_3$ aminoalkyl. RB is selected from among H, $C_1$ to $C_3$ alkyl, or substituted $C_1$ to $C_3$ alkyl. T is selected from among O, S, or is absent and Q is selected from among O, S, or $NR^3$. $R^3$ may be an electron withdrawing group. In one embodiment, $R^3$ is selected from among $C_1$ to $C_6$ alkyl, substituted $C_1$ to $C_6$ alkyl, aryl, substituted aryl, CN, $C(O)R^4$, $SO_2R^4$, SCN, $OR^4$, $SR^4$, $C(O)OR^4$, $C(S)OR^4$, $C(O)SR^4$, or $C(S)SR^4$ and $R^4$ is selected from among $C_1$ to $C_6$ alkyl, substituted $C_1$ to $C_6$ alkyl, aryl, or substituted aryl. In another embodiment, $R^3$ is CN.

RI is located at any position on the ring. In one embodiment, $R^1$ is halogen. In another embodiment, the halogen is bromine. In still another embodiment, $R^1$ is selected from among a substituted benzene ring containing the substituents X, Y and Z as shown below:

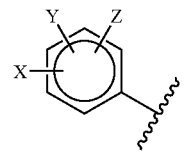

wherein, X is selected from among H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $SO_2NH_2$, $COR^C$, $OCOR^C$, or $NR^DCOR^C$; $R^C$ is selected from among H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl; $R^D$ is selected from among H, $C_1$ to $C_3$ alkyl, or substituted $C_1$ to $C_3$ alkyl; and Y and Z are independently selected from among H, halogen, CN, $NO_2$, amino, aminoalkyl, $C_1$ to $C_3$ alkoxy, $C_1$ to $C_3$ alkyl, or $C_1$ to $C_3$ thioalkoxy.

In another embodiment, $R^1$ is a five or six membered heterocyclic ring comprising 1, 2, or 3 heteroatoms or heteroatom containing groups including O, S, SO, $SO_2$ or $NR_2$ and containing one or two substituents independently selected from among H, halogen, CN, $NO_2$, amino, $C_1$ to $C_3$ alkyl, $C_1$ to $C_3$ alkoxy, $C_1$ to $C_3$ aminoalkyl, $SO_2NH_2$, $COR^E$, or $NR^F$-$COR^E$; $R^E$ is selected from among H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl; and $R^F$ is selected from among H, $C_1$ to $C_3$ alkyl, or substituted $C_1$ to $C_3$ alkyl. $R^2$ is absent or selected from among H, O, or $C_1$ to $C_4$ alkyl. In one embodiment, $R^1$ is a pyrrole ring, or a pyrrole ring having a cyano substituent.

In another embodiment, the following compounds are purified according to the present invention, where A, B, and $R^1$ are as defined above.

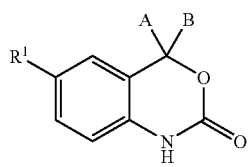 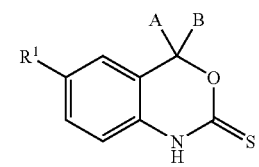

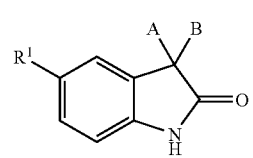 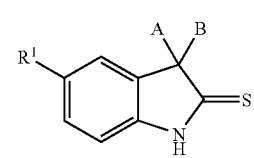

In a further embodiment, the following compounds are purified according to the present invention.

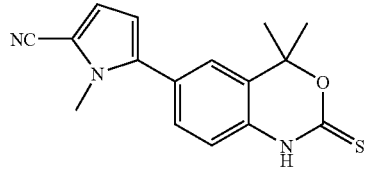
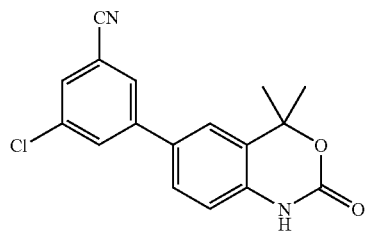
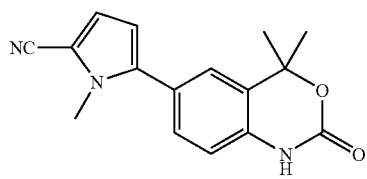
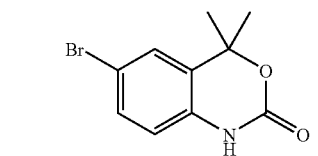
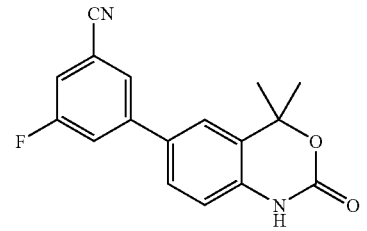
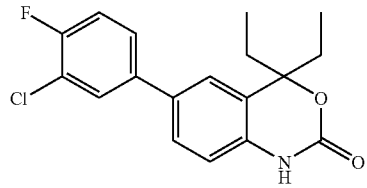
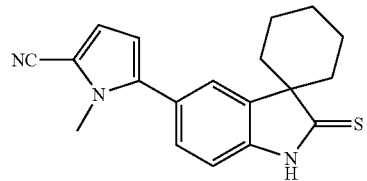
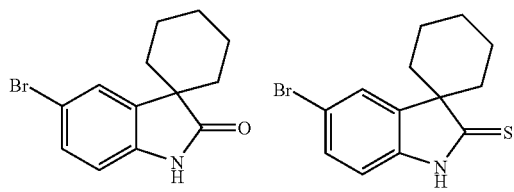

-continued

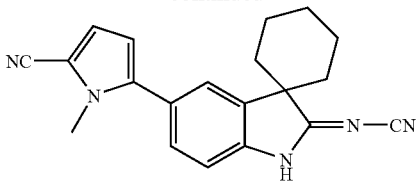

In one embodiment, the compounds produced according to the methods described in U.S. Pat. Nos. 6,509,334; 6,566,358; 6,391,907; 6,608,068; 6,466,648; 6,521,657; 6,583,145; 6,436,929; 6,407,101; 6,562,857; 5,171,851; and 5,874,430; and Singh (*J. Med. Chem.*, 37:248-254 (1994)) are purified according to the method of the invention.

The compounds of the invention are treated with a base in the presence of a purifying solvent to form a basic salt. One of skill in the art would readily be able to select a suitable base according to its basicity and the compound being purified. A number of bases can be used according to the present invention and include hydroxides, alkoxides, amines, amidines, ketones, and amino acids such as arginine, lysine, and betaine, among others. Hydroxides can include, without limitation, 2-hydroxy-N,N,N-trimethylethaminium hydroxide (choline hydroxide), sodium hydroxide, potassium hydroxide, lithium hydroxide, zinc hydroxide, calcium hydroxide, and magnesium hydroxide. Alkoxides can include, without limitation, potassium, sodium, and lithium alkoxides such as potassium tert-butoxide, sodium tert-butoxide, lithium tert-butoxide, sodium methoxide, sodium ethoxide, sodium tert-pentoxide, and potassium tert-pentoxide. Amines can include dimethylamine, diethylamine, piperidine, ethylenediamine, ethanolamine, diethanolamine, triethanolamine, lysine, arginine, morpholine, and tris(hydroxymethyl)aminomethane, among others. In one embodiment, the amine is diethylamine. Amidines can include tetramethylguanidine, diazabicycloundecene, or diazabicyclononene, among others. Ketones can include lower ketones, e.g., of 2 to 7 carbon atoms such as acetone and methyl ethyl ketone.

The inventors have found that when combined with the crude parent compound, diethylamine forms a complex as shown in Scheme 2.

Typically, a molar ratio of 1:1 to 3:1, or greater, base to the crude form of the compound of the invention is utilized. Where desired, the molar ratio is at least about 1.5:1, at least about 2:1, or at least about 3:1. The base can also serve as the solvent for the purification. One of skill in art would readily be able to determine the amount of base required to form the basic salt.

Several purifying solvents can be utilized to form the basic salt and include alcohols, including lower alcohols such as methanol (MeOH), ethanol (EtOH), and isopropanol (*i*PrOH), ethers such as tetrahydrofuran (THF) and 1,2-dimethoxyethane (DME), dimethylsulfoxide (DMSO), dimethylformamide (DMF), N,N-dimethylacetamide, N-methylpyrrolidone, dimethylpyrimidone, or combinations thereof, among others. In one embodiment, the purifying solvent is an alcohol, including a lower alcohol e.g. of 1 to 6 carbon atoms such as methanol (MeOH), ethanol (EtOH), and isopropanol (*i*PrOH), an ether such as tetrahydrofuran (THF), 1,2-dimethoxyethane (DME), or combinations thereof. Water, alone or combined with water-soluble solvents such as alcohols, acetone, or THF; and aqueous solutions of hydroxide salts such as sodium hydroxide, can also be utilized as the solvent. As noted above, the solvent can also be the base utilized to form the basic salt and includes diethylamine, amidine bases, and dimethylamine, optionally under pressure. In a further embodiment, a purifying solvent is selected from among MeOH, THF, and combinations thereof. However, one of skill in the art would readily be able to select a suitable purifying solvent or mixture containing purifying solvent depending on the compound to be purified.

salts with more favorable physical properties than the neutral purified compounds can be utilized as pharmaceutical entities for administration to a patient.

In one embodiment, solid materials present in a solution, including the insoluble basic salts of the invention or insoluble impurities, can be isolated by filtration. However, Scheme 2

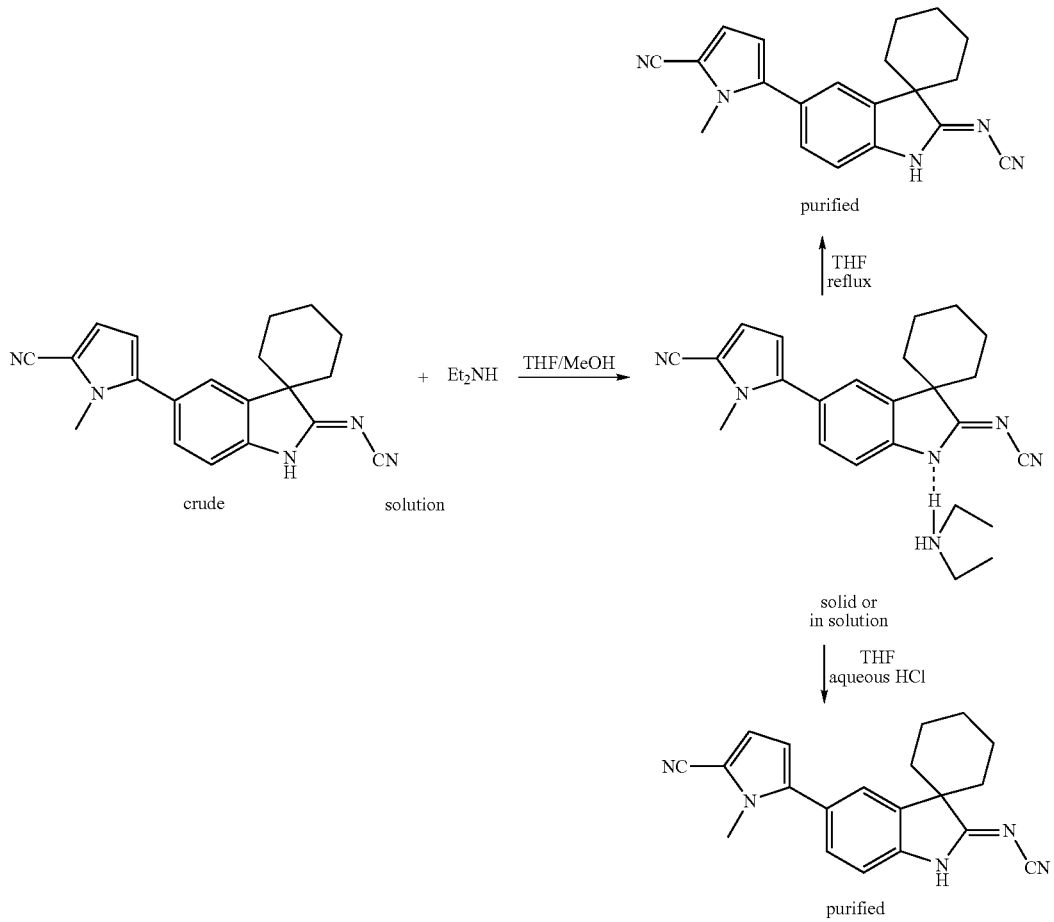

The amount of solvent utilized depends upon the scale of the reaction, i.e., the amount of reagents utilized. One of skill in the art would readily be able to determine the amount of solvent required to purify the indolone, indol-thione, indol-ylidene cyanamide, benzoxazin-one, benzoxazin-thione, benzoxazin-ylidene cyanamide, benzothiazinone, benzothiazine-thione, benzothiazin-ylidene cyanamide compounds, or derivatives thereof.

The basic salts prepared according to the invention can be soluble in the purifying solvent. Any solids can be removed, including unwanted materials that are still present in the purifying solvent after conversion to the soluble basic salt. For example, solid residual heavy metals such as palladium, solid inorganic compounds, and solid organic compounds can be present as impurities and may be removed.

Alternatively, the basic salts of the invention may be insoluble in the purifying solvent. If insoluble, the filtrate lacking the basic salt, but containing any impurities, can then be discarded and the basic salt collected using techniques known to those of skill in the art and thereafter utilized in further reactions or for other purposes. For example, basic one of skill in the art would readily be able to utilize other methods to isolate the solid materials and include, without limitation, centrifugation.

The present invention also provides for converting the basic salt to the purified compound. Methods for converting the basic salt to the purified compound include treatment of the basic salt with water, an acid, or by heat. In one embodiment, the diethylamine basic salts are converted to the purified compound by heating a solution of the same in the purifying solvent such as diethylamine and water.

For conversion of the basic salt that is soluble in the purifying solvent to the purified compound, the purifying solvent containing the soluble basic salt can be treated with water or an acid that neutralizes the basic salt and affects precipitation thereof in the purifying solvent.

If the basic salt is isolated from the purifying solvent as a solid due to its insolubility in the purifying solvent, the basic salt can be dissolved in a solubilizing solvent and thereby precipitated from the solubilizing solvent using water, an acid, or heat. A variety of solubilizing solvents can be used to dissolve basic salts that are not soluble in the purifying solvents utilized to prepare the same. In one embodiment, the solubilizing solvents are polar solvents and include, without limitation, acetone, water, THF, diethylamine, lower alcohols as described above, or combinations thereof. One of skill in the art would readily be able to select a solubilizing solvent for use in dissolving the basic salt according to the present invention.

The temperatures utilized to convert the basic salt to the purified compound must be low enough to avoid decomposition of the basic salt or purified compound and can be readily determined by one of skill in the art. In one embodiment, temperatures of less than the boiling point of the organic or solubilizing solvent are utilized. In another embodiment, the temperature utilized is less than about 100° C.

Once converted to the purified compound, the precipitated purified compound can be isolated using techniques known to those of skill in the art and include filtration and centrifugation, among others.

The purified compound can then be further purified using techniques known to those of skill in the art and include chromatography, distillation, drying, recrystallization, or combinations thereof. In one embodiment, the purified compound can be recrystallized by dissolving the purified compound in a solubilizing solvent as previously described using techniques known to those of skill in the art. In a further embodiment, the purified compound is dissolved in a minimal amount of solubilizing solvent as previously described, the volume of the solution concentrated by removing some of the solubilizing solvent, and the temperature of the solution cooled to promote precipitation of the twice-purified compound. One of skill in the art would readily be able to determine the amount of solubilizing solvent required to recrystallize the purified compound. The twice-purified precipitated compound can then be isolated using techniques as previously discussed.

In another embodiment, the purified compound can be dried at atmospheric pressure or under a vacuum. One of skill in the art would readily be able to select a suitable vacuum to dry the purified compounds. Higher temperatures can also be applied to the purified compound during drying to remove entrapped purifying solvents or solubilizing solvents. Such temperatures can readily be selected by one of skill in the art.

In one embodiment, the present invention therefore provides a method for purifying a compound of formula I:

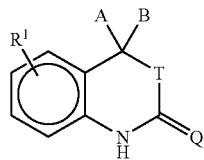

wherein, A and B are independently selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$. In another embodiment, A and B are joined to form a ring comprising (i) a carbon-based 3 to 8 membered saturated spirocyclic ring; (ii) a carbon-based 3 to 8 membered spirocyclic ring containing in its backbone one or more carbon-carbon double bonds; or (iii) a 3 to 8 membered heterocyclic ring containing in its backbone one to three heteroatoms selected from the group consisting of O, S and N, where the rings of (i), (ii) and (iii) are optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)$_2$. $R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl. RB is H, $C_1$ to $C_3$ alkyl, or substituted $C_1$ to $C_3$ alkyl. T is O, S, or absent. Q is O, S, or $NR^3$. $R^3$ is selected from among $C_1$ to $C_6$ alkyl, substituted $C_1$ to $C_6$ alkyl, aryl, substituted aryl, CN, $C(O)R^4$, $SO_2R^4$, SCN, $OR^4$, $SR^4$, $C(O)OR^4$, $C(S)OR^4$, $C(O)SR^4$, or $C(S)SR^4$. $R^1$ can be halogen. $R^1$ can also be a substituted benzene ring containing the substituents X, Y and Z as shown below:

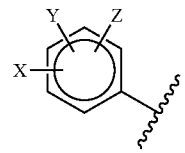

wherein, X is selected from the group consisting of H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $SO_2NH_2$, $COR^C$, $OCOR^C$, and $NR^DCOR^C$. $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl. RD is H, $C_1$ to $C_3$ alkyl, or substituted $C_1$ to $C_3$ alkyl. Y and Z are independently selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy. In another embodiment, $R^1$ is a five or six membered ring having in its backbone 1, 2, or 3 heteroatoms selected from the group consisting of O, S, SO, $SO_2$ and $NR^2$ and containing one or two substituents independently selected from the group consisting of H, halogen, CN, $NO_2$, amino, $C_1$ to $C_3$ alkyl, $C_1$ to $C_3$ alkoxy, $C_1$ to $C_3$ aminoalkyl, $SO_2NH_2$, $COR^E$, and $NR^FCOR^E$. $R^E$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl. $R^F$ is H, $C_1$ to $C_3$ alkyl, or substituted $C_1$ to $C_3$ alkyl. $R^2$ is H, absent, O, or $C_1$ to $C_4$ alkyl. The method includes treating the compound of formula I with a base to form a basic salt; and converting the basic salt to a purified compound of formula I.

In another embodiment, the present invention also provides a method for purifying a compound of formula I:

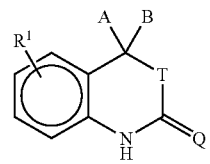

wherein, A and B are independently selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$. In another embodiment, A and B are joined to form a ring comprising (i) a carbon-based 3 to 8 membered saturated spirocyclic ring; (ii) a carbon-based 3 to 8 membered spirocyclic ring containing in its backbone one or more carbon-carbon double bonds; or (iii) a 3 to 8 membered heterocyclic ring containing in its backbone one to three heteroatoms selected from the group consisting of O, S and N, where the rings of (i), (ii) and (iii) are optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)$_2$. $R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl. RB is H, $C_1$ to $C_3$ alkyl, or substituted $C_1$ to $C_3$ alkyl. T is O, S, or absent. Q is O, S, or $NR^3$. $R^3$ is selected from among $C_1$ to $C_6$ alkyl, substituted $C_1$ to $C_6$ alkyl, aryl, substituted aryl, CN, $C(O)R^4$, $SO_2R^4$, SCN, $OR^4$, $SR^4$, $C(O)OR^4$, $C(S)OR^4$, $C(O)SR^4$, or $C(S)SR^4$. In another embodiment, $R^1$ is halogen. In still another embodiment, $R^1$ is a substituted benzene ring containing the substituents X, Y and Z as shown below:

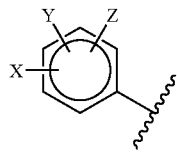

wherein, X is selected from the group consisting of H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $SO_2NH_2$, $COR^C$, $OCOR^C$, and $NR^DCOR^C$. $R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl. $R^D$ is H, $C_1$ to $C_3$ alkyl, or substituted $C_1$ to $C_3$ alkyl. Y and Z are independently selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy. In another embodiment, $R^1$ is a five or six membered ring having in its backbone 1, 2, or 3 heteroatoms selected from the group consisting of O, S, SO, $SO_2$ and $NR^2$ and containing one or two substituents independently selected from the group consisting of H, halogen, CN, $NO_2$, amino, C, to $C_3$ alkyl, $C_1$ to $C_3$ alkoxy, $C_1$ to $C_3$ aminoalkyl, $SO_2NH_2$, $COR^E$, and $NR^FCOR^E$. $R^E$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl. $R^F$ is H, $C_1$ to $C_3$ alkyl, or substituted $C_1$ to $C_3$ alkyl. $R^2$ is H, absent, O, or $C_1$ to $C_4$ alkyl. The method includes mixing the compound of formula I and a solvent; adding a base to the solvent; and precipitating purified compound of formula I using an agent selected from the group consisting of an acid, water, or heat.

III. METHODS OF USING THE PURIFIED COMPOUNDS OF THE INVENTION

The purified compounds of this invention are useful as progesterone receptor modulators, including antagonists and agonists. In one embodiment, the purified compounds of this invention can act as competitive inhibitors of progesterone binding to the PR and therefore act as agonists in functional models, either/or in vitro and in vivo.

The purified compounds are therefore useful as oral contraceptives in both males and females. The purified compounds are also useful in hormone replacement therapy. The purified compounds are further useful in the treatment of endometriosis, luteal phase defects, hormone-dependent neoplastic disease, the synchronization of estrus, and benign breast and prostatic diseases. The hormone-dependent neoplastic disease can include uterine myometrial fibroids, endometriosis, benign prostatic hypertrophy, carcinomas and adenocarcinomas of the endometrium, ovary, breast, colon, prostate, pituitary, uterine, and meningioma. The purified compounds are also useful in treating hirsutism or acne.

In one embodiment, the purified compounds of this invention are used alone as a sole therapeutic agent. In other embodiments, the purified compounds of this invention are used in combination with other agents, such as estrogens, progestins, estrones, or androgens.

The purified compounds of the present invention encompass tautomeric forms of the structures provided herein characterized by the bioactivity of the drawn structures. Further, the purified compounds of the present invention can be used in the form of pharmaceutically acceptable salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminium, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other purified compounds of the invention can be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The purified compounds discussed herein also encompass "metabolites" which are unique products formed by processing the compounds of the invention by the cell or patient. In one embodiment, the metabolites are formed in vivo.

In one embodiment, the purified compounds of this invention are formulated neat. In other embodiments, the purified compounds of the invention are formulated with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

The purified compounds of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. In one embodiment, delivery is oral or transdermal.

In another embodiment, the compositions are delivered orally by tablet, capsule, microcapsules, dispersible powder, granule, suspension, syrup, elixir, and aerosol. In one embodiment, when the compositions are delivered orally, delivery is by tablets and hard- or liquid-filled capsules.

In yet another embodiment, the compositions are delivered intravenously, intramuscularly, subcutaneously, parenterally and intraperitoneally in the form of sterile injectable solutions, suspensions, dispersions, and powders which are fluid to the extent that easy syringe ability exists. Such injectable compositions are sterile, stable under conditions of manufacture and storage, and free of the contaminating action of microorganisms such as bacteria and fungi.

Injectable formations can be prepared by combining the compositions with a liquid. The liquid can be selected from among water, glycerol, ethanol, propylene glycol and polyethylene glycol, oils, and mixtures thereof. In one embodiment, the liquid carrier is water. In another embodiment, the oil is vegetable oil. Optionally, the liquid carrier contains about a suspending agent. In another embodiment, the liquid carrier is an isotonic medium and contains about 0.05 to about 5% suspending agent.

In a further embodiment, the compositions are delivered rectally in the form of a conventional suppository.

In another embodiment, the compositions are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compositions are delivered transdermally or by sustained release through the use of a transdermal patch containing the composition and an optional carrier that is inert to the compound(s), is nontoxic to the skin, and allows for delivery of the purified compound(s) for systemic absorption into the blood stream. Such a carrier can be a cream, ointment, paste, gel, or occlusive device. The creams and ointments can be viscous liquid or semisolid emulsions. Pastes can include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

In one embodiment, sustained delivery devices are utilized in order to avoid the necessity for the patient to take medications on a daily basis. The term "sustained delivery" is used herein to refer to delaying the release of an active agent, i.e., compositions of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314, 206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817, 343). For use in such sustained delivery devices, the compositions of the invention can be formulated as described herein. See, U.S. Pat. Nos. 3,845,770; 3,916,899; 3,536,809; 3,598, 123; and 4,008,719.

The dosage requirements vary with the particular compositions employed, the route of administration, the severity of the symptoms presented and the particular subject being treated. Based on the results obtained in the standard pharmacological test procedures, projected daily dosages of active compound would be about 0.1 to about 500 mg/kg, about 1 to about 100 mg/kg, about 2 to about 80 mg/kg, about 5 to about 50 mg/kg, or about 5 to about 25 mg/kg. Treatment will generally be initiated with small dosages less than the optimum dose of the purified compound. Thereafter the dosage is increased until the optimum effect under the circumstances is reached.

Advantageously, particularly potent PR modulators (e.g., those of formula I) may be useful at the lower end of the dosage ranges provided herein. The dosage regimen may however be adjusted to provide the optimal therapeutic response. For example, several divided doses (e.g., in divided doses 2 to 4 times a day) may be administered daily or the dose may be proportionally reduced as indicated by the exigencies of the therapeutic situation. Alternatively, a single dose can be delivered. In certain embodiments, the delivery can be on a daily, weekly, or monthly basis. In one embodiment, delivery is on a daily basis. Daily dosages can be lowered or raised based on the periodic delivery.

Precise dosages for oral, parenteral, nasal, or intrabronchial administration can be determined by the administering physician based on experience with the individual subject treated. In one embodiment, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

IV. PHARMACEUTICAL KITS

The present invention provides kits or packages of pharmaceutical formulations including the purified compounds of formula I described herein. When the purified compounds of formula I are to be delivered continuously, a package or kit can include the purified compound in each tablet. When the purified compound is to be delivered with periodic discontinuation, a package or kit can include placebos on those days when the purified compound is not delivered.

In one embodiment, the kits are also organized to indicate a single oral formulation or combination of oral formulations to be taken on each day of the cycle. In a further embodiment the kits include oral tablets to be taken on each of the days specified. In still another embodiment, one oral tablet will contain each of the combined daily dosages indicated.

Similarly, other kits of the type described above may be prepared in which a purified compound of formula I is delivered. In one embodiment, the daily dosage of the purified compound of formula I remains fixed in each particular phase in which it is delivered. In a further embodiment, the daily dose units described are to be delivered in the order described, with the first phase followed in order by the second and third phases. In yet another embodiment, the kits contain the placebo described for the final days of the cycle to help facilitate compliance with each regimen.

A number of packages or kits are known in the art for the use in dispensing pharmaceutical agents for oral use. In one embodiment, the package has indicators for each day, and may be a labeled blister package, dial dispenser package, or bottle.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Purification of 5-(4,4-Dimethyl-2-Thioxo-1,4-Dihydro-2H-3,1-Benzoxazin-6-Yl)-1-Methyl-1H-Pyrrole-2-Carbonitrile A slurry of potassium tert-butoxide (126 g) in THF was added to a crude 5-(4,4-dimethyl-2-thioxo-1,4-dihydro-2H-3,1-benzoxazin-6-yl)-1-methyl-1H-pyrrole-2-carbonitrile (171 g; purity 75% HPLC area) dissolved in THF (0.50 L) and cooled to 15° C. More THF (0.25 L) was added and the suspension was stirred for 1 hour, filtered on a Buchner funnel and rinsed with THF (0.50 L). After drying the cake overnight, it was dissolved in a 1:1 acetone:water mixture (0.70 L) at about 5° C. (pH of about 13 to about 14). A 10% aqueous HCl solution (0.35 L) was added dropwise while maintaining the temperature (pH about 3 to about 4). After stirring the suspension for 30 minutes, the stirred suspension was filtered on a Buchner funnel. The cake from the Buchner funnel was washed with water (0.15 and 0.25 L) and dried under vacuum to give the purified product (90.0 g) as a yellow solid (purity >99% HPLC area).

Example 2

Purification of 5-(4,4-Dimethyl-2-Thioxo-1,4-Dihydro-2H-3,1-Benzoxazin-6-Yl)-1H-Methyl-1H-Pyrrole-2-Carbonitrile Crude 5-(4,4-dimethyl-2-thioxo-1,4-dihydro-2H-3,1-benzoxazin-6-yl)-1-methyl-1H-pyrrole-2-carbonitrile (10.0 g), containing 16% of an impurity, was suspended in MeOH (25 mL) followed by addition of potassium tert-butoxide (4.48 g). The suspension was stirred at 65° C. until a clear solution was obtained. Upon cooling to about 5° C., a 4M HCl solution in dioxane (12 mL) was added dropwise. The yellow precipitate was filtered and washed with a 1:1 acetone:water mixture. Recrystallization from an acetone:water mixture yielded 5.4 g of the product containing only 0.5% of the impurity.

Example 3

Purification of 5-(4,4-Dimethyl-2-Thioxo-1,4-Dihydro-2H-3,1-Benzoxazin-6-Yl)-1-Methyl-1H-Pyrrole-2-Carbonitrile Crude 5-(4,4-dimethyl-2-thioxo-1,4-dihydro-2H-3,1-benzoxazin-6-yl)-1-methyl-1H-pyrrole-2-carbonitrile (10.8 g) was stirred in a 1M aqueous NaOH solution (92 mL) for 1 hour. The insoluble material was removed by filtration and the filtrate was slowly added to a solution of MeOH (92 mL) containing acetic acid (5.64 g). The crystalline product was collected via filtration and dried under vacuum at about 50° C. to give 6.95 g (65% yield; purity 96.0% HPLC area).

Example 4

Purification of 5-(4,4-Dimethyl-2-Oxo-1,4-Dihydro-2H-3,1-Benzoxazin-6-Yl)-1-Methyl-1H-Pyrrole-2-Carbonitrile Sodium Salt A suspension of 5-(4,4-dimethyl-2-oxo-1,4-dihydro-2H-3,1-benzoxazin-6-yl)-1-methyl-1H-pyrrole-2-carbonitrile in MeOH or THF, gave solutions upon addition of potassium tert-butoxide, tetramethylguanidine or diazabicycloundecene. The solution in diazabicycloundecene gave the lightest-colored solution. Precipitation of the purified product occurred upon acidification with a 5% aqueous HCl solution.

Substitution of acetic acid for the HCl solution did not result in precipitation of the purified compound.

Example 5

Preparation of 6-Bromo-4,4-Dimethyl-Benzoxazine-2-One Sodium Salt

6-Bromo-4,4-dimethyl-benzoxazine-2-one (2.59 g) was dissolved in THF (50 mL) at ambient temperature followed by addition of sodium tert-butoxide (0.96 g). The mixture was gently heated until a solution was obtained. The solution was evaporated to give a white solid (2.86 g; quant. yield) that was soluble in N-methylpyrrolidone (NMP) and dimethyl pyrimidone (DMPU) heated to about 40 to about 50° C. $^1$H-NMR (DMSO-$d_6$) did not show a peak corresponding to a N—H group.

Example 6

Preparation of 6-Bromo-4,4-Dimethyl-Benzoxazine-2-One Lithium Salt

Similarly, 6-bromo-4,4-dimethyl-benzoxazine-2-one (2.55 g) was reacted with lithium tert-butoxide (10 mL of 1M solution in THF). After evaporation a brownish solid was obtained (3.35 g; quant. yield) that was soluble in dimethyl pyrimidone (DMPU) without heating. $^1$H NMR (DMSO-$d_6$) did not show a peak corresponding to a N—H group.

Example 7

Preparation and Purification of 5-Bromo-Spiro[Cyclohexane-1,3'-[3H]-Indol]-2'(1H)-One 5-Bromo-spiro[cyclohexane-1,3'-[3H]-indol]-2'(1H)-one was prepared from 5-bromooxindole (150 g) using 3 eq. of potassium tert-butoxide in THF at about 0 to about 5° C. Upon completion of the reaction, the reaction mixture containing the potassium salt was quenched with dilute HCl (1 L) to a pH of about 1. The organic layer was washed with brine and distilled to remove some THF. Distillation was continued while acetonitrile was added. The precipitated product was filtered, washed with acetonitrile and dried in a vacuum oven to give 5-bromo-spiro[cyclohexane-1,3'-[3H]-indol]-2'(1H)-one (158 g; 80% yield; purity 98.1% HPLC area).

Example 8

Preparation of 5'-(5-Cyano-1-Methyl-1H-Pyrrol-2-Yl)Spiro[Cyclohexane-1,3'-[3H]Indol]-2'-Ylidenecy Anamide Choline Salt 5'-(5-Cyano-1-methyl-1H-pyrrol-2-yl)spiro[cyclohexane-1,3'-[3H]indol]-2'-ylidenecyanamide (0.96 g) in ethanol (20 mL) was reacted with choline hydroxide (0.91 g; 45% solution in methanol) to form, upon cooling, filtering and drying, 5'-(5-cyano-1-methyl-1H-pyrrol-2-yl)spiro[cyclohexane-1,3'-[3H]indol]-2'-ylidenecyanamide choline salt (0.88 g) as a solid.

The solubility of 5'-(5-cyano-1-methyl-1H-pyrrol-2-yl)spiro[cyclohexane-1,3'-[3H]indol]-2'-ylidenecyanamide choline salt in DMF was 11 mg/mL, while the solubility of 5'-(5-Cyano-1-methyl-1H-pyrrol-2-yl)spiro[cyclohexane-1,3'-[3H]indol]-2'-ylidenecyanamide was 3 mg/mL. Similarly, the melting point of 5'-(5-cyano-1-methyl-1H-pyrrol-2-yl)spiro[cyclohexane-1,3'-[3H]indol]-2'-ylidenecyanamide choline salt was 205.5° C., while the melting point of 5'-(5-Cyano-1-methyl-1H-pyrrol-2-yl)spiro[cyclohexane-1,3'-[3H]indol]-2'-ylidenecyanamide was 270.5-273.5° C.

The choline salt had individual particles of about 5-30 μm. When the choline salt was combined in water to form a slurry, the precipitated material of the parent compound had particles of about 20-50 μm.

The $^1$H-NMR data (DMSO-$d_6$) for the neutral compound (X=H) and salt (X=choline) was obtained and is set forth below in Table 1.

TABLE 1

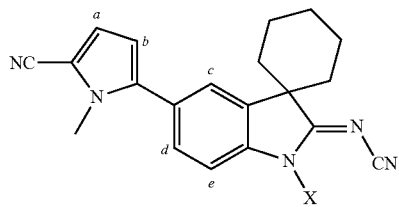

| | $^1$H-NMR chemical shift (ppm) | | | | |
|---|---|---|---|---|---|
| X | $H_a$ | $H_b$ | $H_c$ | $H_d$ | $H_e$ |
| H | 7.02 | 6.33 | 7.71 | 7.41 | 7.17 |
| choline | 6.98 | 6.22 | 7.41 | 7.14 | 6.89 |

Example 9

Purification of 5-(2'-Thioxospiro[Cyclohexane-1,3'-[3H]Indol]-5'-Yl)-1-Methyl-1H-Pyrrole-2-Carbonitrile 5-(2'-Thioxospiro[cyclohexane-1,3'-[3H]indol]-5'-yl)-1-methyl-1H-pyrrole-2-carbonitrile (12.3 g, 98.7% purity) was dissolved in boiling diethylamine (280 mL). A portion of the solvent was distilled off and water (230 mL) was added to form a suspension. The solids were removed via filtration, washed with water and dried at 47° C. in vacuo to give 11.25 g (91.5% yield, 99.1% purity, 0.52% residual diethylamine) of purified product.

Example 10

Comparison of Chemical Shifts of 5'-(5-Cyano-1-Methyl-1H-Pyrrol-2-Yl)Spiro[Cyclohexane-1,3'-[3H]Indol]-2'-Ylidenecyanamide and Salts Thereof 5'-(5-Cyano-1-methyl-1H-pyrrol-2-yl)spiro[cyclohexane-1,3'-[3H]indol]-2'-ylidenecyanamide (0.96 g) in ethanol (20 mL) was reacted with the bases set forth in Table 2 to form, upon cooling, filtering and drying, 5'-(5-cyano-1-methyl-1H-pyrrol-2-yl)spiro[cyclohexane-1,3'-[3H]indol]-2'-ylidenecyanamide salt as a solid. The $^1$H-NMR spectra (DMSO-$d_6$) of the purified compound (X=H) and isolated salts (X=Na, K, choline, and Et$_2$NH·H) were obtained and the data compiled in Table 2.

TABLE 2

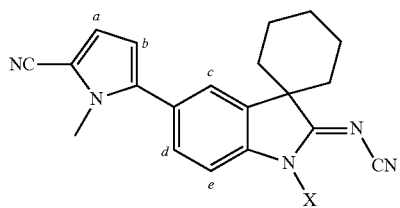

| base | X | $H_a$ | $H_b$ | $H_c$ | $H_d$ | $H_e$ |
|---|---|---|---|---|---|---|
| — | H | 7.02 | 6.33 | 7.71 | 7.41 | 7.17 |
| sodium hydroxide | Na | 6.98 | 6.21 | 7.41 | 7.13 | 6.89 |
| potassium hydroxide | K | 6.97 | 6.21 | 7.42 | 7.14 | 6.93 |
| choline hydroxide | choline | 6.98 | 6.22 | 7.41 | 7.14 | 6.89 |
| $Et_2NH \cdot H$ | | 7.00 | 6.27 | 7.58 | 7.21 | 7.05 |

$^1$H-NMR chemical shift (ppm)

This example illustrates that when diethylamine is utilized as the base, the diethylamine salt produces peaks in the $^1$H-NMR spectra that are not consistent with the peaks for the neutral parent compound or the sodium, potassium, or choline salts. Specifically, the peaks in the $^1$H-NMR spectrum for the diethylamine salt are at chemical shifts between the neutral and sodium, potassium, or choline salts.

Example 11

Preparation of 5-(2'-Thixoxspiro[Cyclohexane-1,3'-[3H]Indol]-5'-Yl)-1-Methyl-1H-Pyrrole-2-Carbonitrile Sodium Salt 5-(2'-Thioxospiro[cyclohexane-1,3'-[3H]indol]-5'-yl)-1-methyl-1H-pyrrole-2-carbonitrile (0.72 g) was dissolved in THF (10 mL) at ambient temperature. One mL of this solution was mixed with aqueous 1N NaOH (0.22 mL). Evaporation and trituration with heptane gave 5-(2'-thioxospiro[cyclohexane-1,3'-[3H]indol]-5'-yl)-1-methyl-1H-pyrrole-2-carbonitrile sodium salt as a solid (mp 83.4° C.).

Example 12

Preparation of 5-(2'-Thixoxspiro[Cyclohexane-1,3'-[3H]Indol]5'-Yl)-1-Methyl-1H-Pyrrole-2-Carbonitrile Choline Salt 5-(2'-Thioxospiro[cyclohexane-1,3'-[3H]indol]-5'-yl)-1-methyl-1H-pyrrole-2-carbonitrile (0.72 g) was dissolved in THF (10 mL) at ambient temperature. One mL of this solution was mixed with aqueous 1N choline hydroxide (62.1 mg, 45% solution in MeOH). Evaporation and trituration with heptane gave 5-(2'-thioxospiro[cyclohexane-1,3'-[3H]indol]-5'-yl)-1-methyl-1H-pyrrole-2-carbonitrile sodium salt as a solid (mp 159° C.).

Example 13

Preparation of 5-(2'-Thioxospiro[Cyclohexane-1,3'-[3H]Indol]5'-Yl)-1-Methyl-1H-Pyrrole-2-Carbonitrile Potassium Salt (i) Procedure A
5-(2'-Thioxospiro[cyclohexane-1,3'-[3H]indol]-5'-yl)-1-methyl-1H-pyrrole-2-carbonitrile (0.72 g) was dissolved in THF (10 mL) at ambient temperature. One mL of this solution was mixed with potassium tert-butoxide (25.3 mg). Evaporation and trituration with heptane gave 5-(2'-thioxospiro[cyclohexane-1,3'-[3H]indol]-5'-yl)-1-methyl-1H-pyrrole-2-carbonitrile sodium salt as a solid (mp 79.2° C.).

(ii) Procedure B
5-(2'-Thioxospiro[cyclohexane-1,3'-[3H]indol]-5'-yl)-1-methyl-1H-pyrrole-2-carbonitrile (0.163 g) was suspended in acetone (3 mL). Anhydrous 325 mesh potassium carbonate (0.726 g) was added and the mixture was stirred under nitrogen overnight. The stirred mixture was filtered, washed with acetone (5 mL) and the filtrate evaporated to give 5-(2'-thioxospiro[cyclohexane-1,3'-[3H]indol]-5'-yl)-1-methyl-1H-pyrrole-2-carbonitrile potassium salt (0.185 g) as a solid. $^1$H-NMR (DMSO-$d_6$, ppm): (absent N—H), 7.64, 7.25, 7.05, 7.0, 6.27, 3.72, 2.1-1.65, and 1.1-1.0.

Example 14

Purification of 5-(2'-Thioxospiro[Cyclohexane-1,3'-[3H]Indol]-5'-Yl)-1-Methyl-1H-Pyrrole-2-Carbonitrile Via its Sodium Salt Crude 5-(2'-thioxospiro[cyclohexane-1,3'-[3H]indol]-5'-yl)-1-methyl-1H-pyrrole-2-carbonitrile (1.0 g, purity 97.3% HPLC area) was suspended in acetone (6.6 mL) and water (2 mL). Sodium hydroxide (0.33 g, 50% solution in water) was added and the mixture was warmed to 32-35° C. for 15 min. The warmed solution was filtered, diluted with water (2 mL) and cooled to 5-10° C. The cooled solution was then neutralized with aqueous HCl to a pH of 5-7, stirred for 30 minutes, filtered and washed with a mixture of acetone-water (1:1) to give purified 5-(2'-thioxospiro[cyclohexane-1,3'-[3H]indol]-5'-yl)-1-methyl-1H-pyrrole-2-carbonitrile (0.97 g, purity 98.7% HPLC area). $^1$H NMR (DMSO-$d_6$, ppm): 12.75 (N—H), 7.82, 7.44, 7.15, 7.04, 6.35, 3.72, 2.0-1.7, and 1.4-1.3.

Example 15

Purification of 5-(2'-Thioxospiro[Cyclohexane-1,3'-[3H]Indol]-5'-Yl)-1-Methyl-1H-Pyrrole-2-Carbonitrile Via its Cesium Salt 5-(2'-Thioxospiro[cyclohexane-1,3'-[3H]indol]-5'-yl)-1-methyl-1H-pyrrole-2-carbonitrile (0.204 g, 96.8% HPLC area) was heated to reflux with cesium carbonate (0.419 g) in ethanol SDA3 (5 mL) to form a clear solution. Water (5 mL) was added, followed by concentrated HCl (0.3 mL) to a pH of 6. The obtained solids were filtered, washed with water (3 mL) and dried to give purified 5-(2'-thioxospiro[cyclohexane-1,3'-[3H]indol]-5'-yl)-1-methyl-1H-pyrrole-2-carbonitrile (0.176 g, 99.0% HPLC area).

Example 16

Purification of 5'-(5-Cyano-1-Methyl-1H-Pyrrol-2-Yl)Spiro[Cyclohexane-1,3'-[3H]Indol]-2'-Ylidenecyanamide Via its Potassium Salt Crude 5'-(5-cyano-1-methyl-1H-pyrrol-2-yl)spiro[cyclohexane-1,3'-[3H]indol]-2'-ylidenecyanamide (2.7 g; purity 90% HPLC area) was dissolved in DMSO (11 mL) at 60-70° C., followed by addition of isopropanol (30 mL). After cooling the suspension to 10° C., the cooled suspension was filtered and washed with isopropanol. The resultant wet cake containing residual DMSO was suspended in isopropanol (10 mL) and potassium tert-butoxide (1.9 g) was added. The resultant clear solution was cooled to 5-15° C. and acidified with 10% HCl to a pH of 3-4 to form a suspension. The suspension was filtered and washed with water until a sample of the filtrate was found to be neutral according to pH. The obtaining solids were dried in vacuo to give purified 5'-(5-cyano-1-methyl-1H-pyrrol-2-yl)spiro[cyclohexane-1,3'-[3H]indol]-2'-ylidenecyanamide (1.8 g, 67% yield based on the crude; purity 98.9% HPLC area; DMSO 0.008%).

Example 17

Depletion of Residual Palladium from 5'-(5-Cyano-1-Methyl-1H-Pyrrol-2-Yl)Spiro[Cyclohexane-1,3'-[3H]Indol]-2'-Ylidenecyanamide Via its Potassium Salt Crude 5'-(5-cyano-1-methyl-1H-pyrrol-2-yl)spiro[cyclohexane-1,3'-[3H]indol]-2'-ylidenecyanamide (1.0 g) containing residual Pd (5100 ppm) was suspended in THF (5 mL). Upon addition of aqueous 1M KOH (5 mL), a clear orange solution was obtained. N-Acetylcysteine (1.3 g) was added, the mixture was stirred for 1 hour, and filtered. Ten percent aqueous HCl (3 mL) was added dropwise to the filtrate causing precipitation of a white solid. The solution was filtered, the solid washed with methanol, and the washed solid dried to give 5'-(5-cyano-1-methyl-1H-pyrrol-2-yl)spiro[cyclohexane-1,3'-[3H]indol])-2'-ylidenecyanamide (0.6 g; 60% yield; 96 ppm Pd).

Example 18

Preparation of 5'-(5-Cyano-1-Methyl-1H-Pyrrol-2-Yl)Spiro[Cyclohexane-1,3'-[3H]Indol]-2'-Ylidenecyanamide Diethylamine Salt/Complex 5'-(5-Cyano-1-methyl-1H-pyrrol-2-yl)spiro[cyclohexane-1,3'-[3H]indol]-2'-ylidenecyanamide (16 g) in THF (100 mL) was treated with diethylamine (37 g) and refluxed until a solution was obtained. Upon cooling to ambient temperature, a white precipitate was formed. The solution was filtered, the precipitate washed with THF and dried to give 18.0 g (90% yield) of the diethylamine salt/complex. $^1$H NMR (DMSO-$d_6$, ppm): 7.58, 7.21, 7.05, 7.00, 6.5-6 (br), 6.27, 3.71, 2.80 (q), 1.9-1.7, 1.5-1.4, and 1.10 (t).

Example 19

Purification of 5'-(5-Cyano-1-Methyl-1H-Pyrrol-2-Yl)Spiro[Cyclohexane-1,3'-[3H]Indol]-2'-Ylidenecyanamide Via its Diethylamine Salt/Complex Crude 5'-(5-cyano-1-methyl-1H-pyrrol-2-yl)spiro[cyclohexane-1,3'-[3H]indol]-2'-ylidenecyanamide (95.0 g; purity 78% HPLC area) in THF (250 mL) was treated with diethylamine (105 g) and refluxed with a concomitant addition of THF (3.35 L) until dissolved. The solvent was distilled off (2.5 L) during which a precipitate was formed. The flask was cooled to ambient temperature and the white precipitate was filtered, washed with ether and dried to give 58.0 g (61% yield) of purified 5'-(5-cyano-1-methyl-1H-pyrrol-2-yl)spiro[cyclohexane-1,3'-[3H]indol])-2'-ylidenecyanamide (purity >99% HPLC area).

All publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:
1. A method for purifying a compound of formula I:

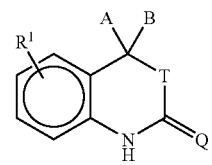

wherein:
A and B are independently selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$; or
A and B are joined to form a ring comprising (i), (ii), or (iii):
(i) a carbon-based 3 to 8 membered saturated spirocyclic ring;
(ii) a carbon-based 3 to 8 membered spirocyclic ring containing in its backbone one or more carbon-carbon double bonds; or
(iii) a 3 to 8 membered heterocyclic ring containing in its backbone one to three heteroatoms selected from the group consisting of O, S and N;
the rings of (i), (ii) and (iii) being optionally substituted by from 1 to 4 groups selected from the group consisting of fluorine, $C_1$ to $C_6$ alkyl, $C_1$ to $C_6$ alkoxy, $C_1$ to $C_6$ thioalkyl, $CF_3$, OH, CN, $NH_2$, $NH(C_1$ to $C_6$ alkyl), and $N(C_1$ to $C_6$ alkyl)$_2$;
$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;
$R^B$ is H, $C_1$ to $C_3$ alkyl, or substituted $C_1$ to $C_3$ alkyl;
T is O or S;
Q is O, S, or $NR^3$;
$R^1$ is (iv), (v), or (vi):
(iv) halogen;
(v) a substituted benzene ring containing the substituents X, Y and Z as shown below:

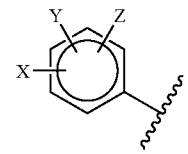

wherein:
X is selected from the group consisting of H, halogen, CN, $C_1$ to $C_3$ alkyl, substituted $C_1$ to $C_3$ alkyl, alkenyl, substituted alkenyl, alkynyl, substituted alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $SO_2NH_2$, $COR^C$, $OCOR^C$, and $NR^DCOR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^D$ is H, $C_1$ to $C_3$ alkyl, or substituted $C_1$ to $C_3$ alkyl;

Y and Z are independently selected from the group consisting of H, halogen, CN, $NO_2$, amino, aminoalkyl, $C_1$ to $C_3$ alkoxy, $C_1$ to $C_3$ alkyl, and $C_1$ to $C_3$ thioalkoxy; or (vi) a five or six membered ring having in its backbone 1, 2, or 3 heteroatoms selected from the group consisting of O, S, SO, $SO_2$ and $NR^2$ and containing one or two substituents independently selected from the group consisting of H, halogen, CN, $NO_2$, amino, $C_1$ to $C_3$ alkyl, $C_1$ to $C_3$ alkoxy, $C_1$ to $C_3$ aminoalkyl, $SO_2NH_2$, $COR^E$, and $NR^FCOR^E$;

$R^E$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^F$ is H, $C_1$ to $C_3$ alkyl, or substituted $C_1$ to $C_3$ alkyl;

$R^2$ is H, absent, O, or $C_1$ to $C_4$ alkyl; and $R^3$ is $C_1$ to $C_6$ alkyl, substituted $C_1$ to $C_6$ alkyl, aryl, substituted aryl, CN, $C(O)R^4$, $SO_2R^4$, SCN, $OR^4$, $SR^4$, $C(O)OR^4$, $C(S)OR^4$, $C(O)SR^4$, or $C(S)SR^4$;

$R^4$ is $C_1$ to $C_6$ alkyl, substituted $C_1$ to $C_6$ alkyl, aryl, or substituted aryl; wherein said method comprises:

(a) treating a crude form of a compound of formula I with a base in the presence of a solvent to form a basic salt; and (b) converting said basic salt to a purified form of a compound of formula I.

2. The method according to claim 1, wherein said compound of formula I is selected from the group consisting of an indol-2-one, indol-2-thione, indol-2-ylidene cyanamide; benzoxazine-2-one, benzoxazine-2-thione, benzoxazin-2-ylidene cyanamide; benzothiazin-2-one, benzothiazine-2-thione, and a benzothiazin-2-ylidene cyanamide.

3. The method according to claim 1, wherein said solvent is selected from the group consisting of tetrahydrofuran, methanol, diethylamine, acetone, and water.

4. The method according to claim 1, wherein said base is selected from the group consisting of an alkoxide salt, diethylamine, a hydroxide salt, tetramethylguanidine, and diazabicycloundecene.

5. The method according to claim 1, wherein said basic salt is soluble in said solvent.

6. The method according to claim 1, wherein said basic salt is insoluble in said solvent.

7. The method according to claim 1, further comprising isolating said basic salt.

8. The method according to claim 7, wherein said isolated basic salt is dissolved in a solubilizing solvent.

9. The method according to claim 8, wherein said solubilizing solvent is acetone or aqueous acetone.

10. The method according to claim 1, further comprising filtering the product of step (a).

11. The method according to claim 1, wherein said purified compound of formula I is precipitated.

12. The method according to claim 11, wherein said precipitation is performed using an acid.

13. The method according to claim 12, wherein said acid is an organic acid or a mineral acid.

14. The method according to claim 11, wherein said precipitation is performed using water.

15. The method according to claim 11, wherein said precipitation is performed using heat.

16. The method according to claim 1, wherein said step (b) comprises treating said basic salt with an agent that converts said basic salt to said purified compound of formula I.

17. The method according to claim 16, wherein said agent is selected from the group consisting of water, an acid, and heat.

18. The method according to claim 1, further comprising isolating said purified compound of formula I.

19. The method according to claim 1, further comprising recrystallizing said purified compound of formula I.

20. The method according to claim 1, wherein said compound of formula I is selected from the group consisting of 5-(4,4-dimethyl-2-oxo-1,4-dihydro-benzoxazin)-1-methyl-1H-pyrrole-2-carbonitrile, 5-(4,4-dimethyl-2-oxo-1,4-dihydro-benzoxazin)-3-chloro-benzonitrile, 5-(4,4-dimethyl-2-thioxo-1,4-dihydro-benzoxazin)-1-methyl-1H-pyrrole-2-carbonitrile, 6-bromo-4,4-dimethyl-1,4-dihydro-benzoxazin-2-one, 5-(4,4-dimethyl-2-oxo-1,4-dihydro-benzoxazin)-3-fluoro-benzonitrile, and 5-(4,4-diethyl-2-oxo-1,4-dihydro-benzoxazin)-3-chloro-4-fluoro-benzonitrile.

21. The method according to claim 1, wherein said basic salt is selected from the group consisting of 5-(4,4-dimethyl-2-oxo-1,4-dihydro-2H-3,1-benzoxazin-6-yl)-1-methyl-1H-pyrrole-2-carbonitrile sodium salt, 6-bromo-4,4-dimethyl-benzoxazin-2-one sodium salt, and 6-bromo-4,4-dimethyl-benzoxazin-2-one lithium salt.

* * * * *